US012714407B2

(12) United States Patent
Forsvall et al.

(10) Patent No.: US 12,714,407 B2
(45) Date of Patent: Aug. 25, 2026

(54) NEEDLE SYSTEM FOR INJECTION AND ASPIRATION

(71) Applicant: Xaga Surgical AB, Helsingborg (SE)

(72) Inventors: Andreas Forsvall, Helsingborg (SE); Krister Uvnäs, Södra Sandby (SE); Mats Edberg, Eslöv (SE); Erik Sparre, Malmö (SE)

(73) Assignee: Xaga Surgical AB, Helsingborg (SE)

( * ) Notice: Subject to any disclaimer, the term of this patent is extended or adjusted under 35 U.S.C. 154(b) by 1055 days.

(21) Appl. No.: 17/775,510

(22) PCT Filed: Nov. 5, 2020

(86) PCT No.: PCT/EP2020/081083
§ 371 (c)(1),
(2) Date: May 9, 2022

(87) PCT Pub. No.: WO2021/089677
PCT Pub. Date: May 14, 2021

(65) Prior Publication Data

US 2022/0387007 A1 Dec. 8, 2022

(30) Foreign Application Priority Data

Nov. 8, 2019 (EP) .................................... 19207890

(51) Int. Cl.
*A61M 5/32* (2006.01)
*A61B 10/02* (2006.01)

(52) U.S. Cl.
CPC ........... *A61B 10/0283* (2013.01); *A61M 5/32* (2013.01); *A61M 5/329* (2013.01); *A61M 5/3286* (2013.01)

(58) Field of Classification Search
CPC .. A61M 5/3293; A61M 5/3234; A61M 5/343; A61M 1/774; A61M 25/0069; A61M 25/0075; A61M 5/3286
See application file for complete search history.

(56) References Cited

U.S. PATENT DOCUMENTS

| | | | |
|---|---|---|---|
| 5,335,671 | A | 8/1994 | Clement |
| 10,076,323 | B2 | 9/2018 | Smith et al. |

(Continued)

FOREIGN PATENT DOCUMENTS

| | | | | |
|---|---|---|---|---|
| EP | 2882347 A1 | 6/2015 | | |
| JP | 2019-531165 | 10/2019 | | |
| WO | WO-2018028837 A1 * | 2/2018 | ......... | A61B 10/0048 |

OTHER PUBLICATIONS

European Patent Office; International Search Report and Written Opinion for PCT application No. PCT/EP2020/081083; Dec. 4, 2020; entire document.

*Primary Examiner* — Courtney Fredrickson
*Assistant Examiner* — Kayla M. Turkowski
(74) *Attorney, Agent, or Firm* — Shore IP Group, PLLC; Howard J. Klein

(57) ABSTRACT

A needle system includes a needle arrangement having a hollow needle with a distal end opening, and a proximal end connected to an actuator body of an actuator device, and open to a cavity in the actuator body that has a changeable volume. The needle arrangement includes a rod with a distal tip and a shaft portion fits inside the needle. The cavity has an opening configured to interface with a fluid transportation device for allowing fluid into and/or out of the cavity for injecting and/or aspirating fluid through the needle. The rod tip is configured to seal the needle opening, and to unseal the needle opening when the rod is shifted distally relative to the needle. The rod interacts with the actuator device such that (Continued)

a change in volume of the cavity forces the rod in a distal direction to unseal the needle opening.

18 Claims, 5 Drawing Sheets

(56) References Cited

U.S. PATENT DOCUMENTS

| | | | | |
|---|---|---|---|---|
| 10,828,101 | B2 | 11/2020 | Germain et al. | |
| 11,583,272 | B2 | 2/2023 | Smith et al. | |
| 11,583,335 | B2 | 2/2023 | Germain et al. | |
| 11,701,474 | B2 | 7/2023 | Forsvall | |
| 2009/0043278 | A1* | 2/2009 | Tanaka ................ | A61M 5/1452<br>604/138 |
| 2009/0326412 | A1* | 12/2009 | Pakter ................ | A61B 10/0266<br>600/567 |
| 2011/0190661 | A1 | 8/2011 | Wegener | |
| 2019/0175842 | A1 | 6/2019 | Forsvall | |

* cited by examiner

NEEDLE SYSTEM FOR INJECTION AND ASPIRATION

CROSS-REFERENCE TO RELATED APPLICATIONS

This application is the § 371 National Stage Entry of International Application No. PCT/EP2020/081083, filed on Nov. 5, 2020, which claims the benefit of European Patent Application No. 19207890.5, filed on Nov. 8, 2019, the contents of which applications are herein incorporated by reference in their entirety.

FIELD OF THE INVENTION

Embodiments herein relate to a needle system comprising a needle and an actuator device, the needle system being capable of injection and/or aspiration of fluids.

BACKGROUND OF THE INVENTION

Within the field of medicine, needle arrangements for various purposes exist, for example needle arrangements for taking biopsy samples. A biopsy sampling arrangement includes, typically, in addition to a needle arrangement also some kind of actuator device that facilitates for an operator to push the biopsy needle into tissue and cut a biopsy sample of tissue. An important issue when performing biopsy sampling is, of course, to safeguard against accidental damage to a patient and to minimize the risks of infection.

Several examples of risk situations exist. When punctuating through a mucus membrane surface sterilisation is not possible and current standard needles will bring bacteria into tissue as exemplified in administration of local anaesthesia prior to transrectal prostate biopsy. Skin can be sterilized with for example an alcohol. However, crypts in the skin may still harbour bacteria. A standard needle puncture may bring the bacteria into tissue, in special situations causing clinical infection. Examples includes situations where the target for the needle is extremely vulnerable such as in amniocentesis or puncture into foreign subcutaneous devices such as subcutaneous venous ports or shunts. Other examples are when the patient is very sensitive to infections, such as any puncture in diabetics or in patients with ongoing cytostatic or other immune modeling treatments. Prior art needles have, typically, an open tip and acts as a punch that carries bacteria and parts of tissue into the body, which is a perfect seedbed for infection.

Closed needles may overcome part of these problems but prior art needles lacks the design and functional mechanisms that ensures minimization of bacterial transfer, as well as the ability to safely be used multiple times, being user independent in its function as well as supplying the tactical feedback into the hands of the user given by todays standard hypodermic needle where you can feel the resistance in the tissue both in injection and aspiration.

SUMMARY OF THE INVENTION

In view of the above, an object of the present disclosure is to overcome drawbacks related to prior art injection and aspiration needle systems.

This object is achieved in a first aspect by a needle system comprising a needle arrangement and an actuator device. The needle arrangement comprises needle and a rod. The needle has a proximal end and a distal end and a needle opening at the distal end of the needle. The rod has a proximal end and a distal end and a length that is greater than the length of the needle. The rod comprises an elongated rod shaft portion configured to fit inside the needle and a rod tip portion located at the distal end of the rod. The actuator device comprises an actuator body comprising a cavity and a first opening configured to interface with a fluid transportation device to allow fluid into and/or out of the cavity and thereby allowing fluid to be injected and/or aspirated through the needle.

The needle system has a closed state and an open state. The rod tip portion seals, or blocks, the needle opening in the closed state, and the rod tip portion is shifted forward relative to the needle and unseals, or unblocks, the needle opening in the open state. The proximal end of the needle is connected to the actuator body and the proximal end of the needle is open to the cavity. The rod is configured to interact with the actuator device such that at a change of volume of the cavity, a force is exerted on the rod in a distal direction, setting the needle arrangement in the open state.

It is to be noted that the concept of fluid transportation device is to be interpreted broadly and include any device capable of perform aspiration and/or injection, including any kind of syringe, tube or vessel, infusion aggregates with IV-fluid units, independently configured with an over- or under-pressure or connected to a device that generates an over- or under-pressure relative to a surrounding atmosphere pressure.

Such a needle system overcomes drawbacks of prior art needle systems and it is simple in terms of operation while at the same time being capable of injection as well as aspiration.

In various embodiments, the rod is configured to interact with a distal wall of the cavity. For example, the actuator device may in some embodiments comprise a flexible distal membrane arranged at a distal end of the cavity and constituting the distal wall of the cavity. In such embodiments, the rod may be configured to interact with the distal membrane such that when the cavity is pressurized with respect to the outside of the cavity, a force is exerted on the rod by the distal membrane in a distal direction, setting the needle system in the open state.

In various embodiments, the rod is configured to interact with a proximal wall of the cavity. For example, the actuator device may in some embodiments comprise a flexible proximal membrane arranged at a proximal end of the cavity and constituting the proximal wall of the cavity. In such embodiments, the rod may be configured to interact with the proximal membrane such that when the cavity is de-pressurized with respect to the outside of the cavity, a force is exerted on the rod by the proximal membrane in the distal direction, setting the needle system in the open state.

In other words, embodiments of such a needle system comprise an actuator device that has either a distal or a proximal membrane that is capable of flexing, and thereby increasing or decreasing the volume of the cavity, and as a consequence push the rod distally to open the needle system into the open state and thereby enabling transfer of fluid from or to a fluid transportation device interfacing with the system.

Furthermore, such configurations have an advantage that an overpressure (relative to a surrounding atmosphere pressure) present inside a system with only a proximal configuration and, conversely, an under-pressure (relative to a surrounding atmosphere pressure) present inside a system with only a distal configuration will not risk an undesired opening of the system. This may be advantageous when only injection or only aspiration is sought, and protection is needed from the opposite.

In some embodiments, the actuator device may comprise a distal flexible membrane arranged at a distal end of the cavity and constituting the distal wall of the cavity, and a proximal flexible membrane arranged at a proximal end of the cavity and constituting the proximal wall of the cavity. In such embodiments, the rod may be configured to interact with the distal membrane such that when the cavity is pressurized with respect to the outside of the cavity, a force is exerted on the rod by the distal membrane in a distal direction, setting the needle system in the open state and configured to interact with the proximal membrane such that when the cavity is de-pressurized with respect to the outside of the cavity, a force is exerted on the rod by the proximal membrane in the distal direction, setting the needle system in the open state.

In other words, embodiments of such a needle system comprise an actuator device that has both a distal or a proximal membrane that is capable of flexing, and thereby increasing and decreasing the volume of the cavity, and as a consequence push the rod distally to open the needle system into the open state and thereby enabling transfer of fluid from and to a fluid transportation device interfacing with the system.

In various embodiments, the actuator device may comprise a spring arranged inside the actuator body, the spring being arranged to provide a force in the proximal direction on the rod and thereby to bias the needle system in the closed state.

By biasing the rod proximally, the tip portion of the rod is held firmly against the needle opening. Such a configuration prevents any gap to open up between the needle opening and the tip portion of the rod during insertion and retraction of the needle. Consequently, unwanted collection of, e.g., bacteria on the needle is minimized during insertion and retraction.

It is to be noted that the term spring is to be interpreted broadly and it includes any device capable of providing a spring force, for example an injection moulded plastic detail, and although the present disclosure exemplifies spring by a coiled spring, it is to be understood that any other device may be used that provides a corresponding spring force.

Furthermore, such a configuration allows variation, adjustment and optimization of the relationship between spring force and the characteristics of the membrane. Thereby is possible, to a very accurate level, to re-create the tactile feeling that a user of a conventional needle experiences. Such a tactile feeling experienced by a user represents the resistance met by the injection or aspiration fluid and, needless to say, represents a very important or even crucial aspect of both injection and aspiration in living tissue in order to avoid injury.

Moreover, by biasing the rod proximally it will automatically close when the needle system is not active in performing injection or aspiration, making the safety system user independent as well as protecting from unintended opening of the needle when moved in tissue.

Furthermore, during injection there is always a overpressure (relative to a surrounding atmosphere pressure) around the tip portion and this fact, in combination with the fact that the rod is biased, makes the needle system to close gradually as the overpressure from the fluid transportation device decreases, which in turn minimizes or at least decreases the risk of tissue being caught in a gap between the tip portion and the needle opening, which enables a complete closure of the needle system such that the tip portion abuts the needle opening. This creates a needle system that maintains its antibacterial features even after injection making it safe for multiple injections in the same patient, for example in deposition of local anaesthesia around the prostate prior to prostate biopsy.

Optimizing the fit between the needle and the sheath with for example a rear facing internal central cone guides the tip to centre in the sheath upon closure. Using the same outer diameter for the needle tip and the sheath creates a smooth outer surface without gaps or edges. The combination of biasing the needle tip, an optimal fit and a smooth outer surface creates a needle with a lowered probability of collecting bacteria in both single and multiple use. This effect can be further enhanced by for example polishing of the surface and/or coatings.

The cavity inside the actuator device may have a spatial extent defined as the proximal end of the cavity having a first diameter in a direction perpendicular to the distal and proximal directions, the distal end of the cavity having a second diameter in the direction perpendicular to the distal and proximal directions, and a third diameter of the cavity, in the direction perpendicular to the distal and proximal directions, at a position between the distal end and the proximal end of the cavity, said third diameter being smaller than the first diameter and smaller than the second diameter.

Such a configuration of the cavity minimizes the volume of the cavity and thereby minimizes the volume of any fluid that will remain in the cavity subsequent to injection and/or aspiration. This is advantageous for example in that it ensures that the correct volume of fluid can be administered and also in terms of cost due to the fact that many fluids for injection are very expensive. Also, by minimizing the remaining fluid subsequent to aspiration, more of the fluid aspirated can be used for analysis and a minimization can be obtained of the amount of fluid necessary to be aspirated from, e.g., a person.

In some embodiments, the needle system, a flexible bellows is arranged within the actuator body and forms the cavity. Such a bellows may comprise a distal bellows wall and a proximal bellows wall. A rod carrier to which the rod is attached may be arranged partly within the cavity and the rod may be configured to interact via the rod carrier with the distal wall and the proximal wall of the bellows such that, during both injection and aspiration, the rod is forced in the distal direction setting the needle system in the open state.

Such embodiments are advantageous in that they are simple, both in terms of a low number of components as well as in terms of being simple to assemble and thereby being efficient in terms of manufacturing and assembly costs.

DETAILED DESCRIPTION OF PREFERRED EMBODIMENT

Figure 1A:
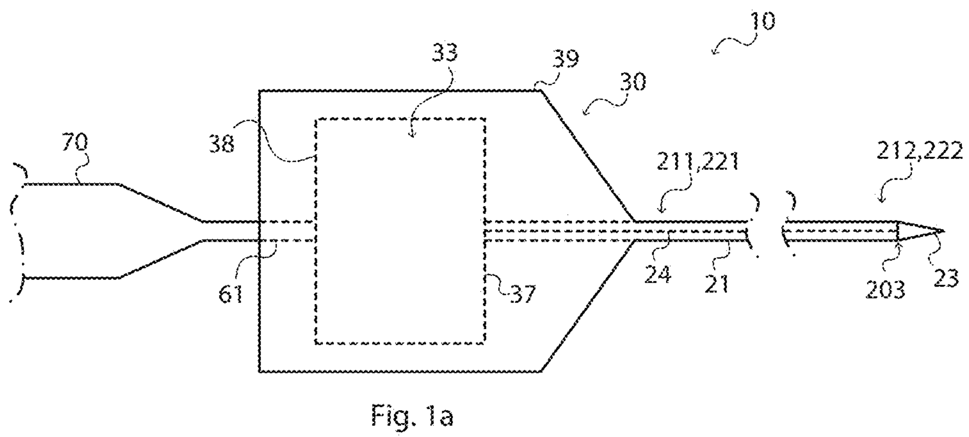
FIG. 1*a* schematically illustrates a needle system.

FIG. 1*a* schematically illustrates a needle system 10 comprising a needle arrangement 20 and an actuator device 30. The needle arrangement 20 comprises a needle 21 and a rod 24. The needle 21 has a proximal end 211, a distal end 212 and a needle opening 203 at the distal end 212 of the needle 21.

The rod 24 has a proximal end 221 and a distal end 222 and it has a length that is greater than the length of the needle 21. The rod 24 comprises an elongated rod shaft portion 26 configured to fit inside the needle 21 and a rod tip portion 23 located at the distal end 222 of the rod 24.

The actuator device 30 comprises an actuator body 39 comprising a cavity 33, a first opening 61 configured to interface with a fluid transportation device 70 to allow fluid into and/or out of the cavity 33 and thereby allowing fluid to be injected and/or aspirated through the needle 21. The concept of fluid transportation device is to be interpreted broadly and include any device capable of perform aspiration and/or injection, including any kind of syringe, tube or vessel.

Figure 1B:
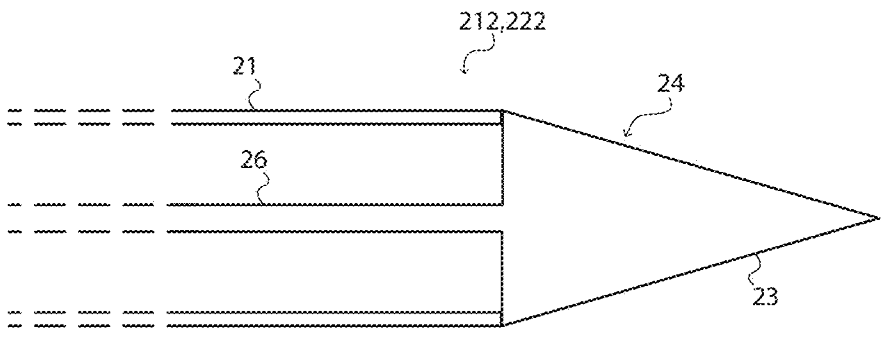
FIG. 1*b* schematically illustrates a needle system in a closed state.
Figure 1C:
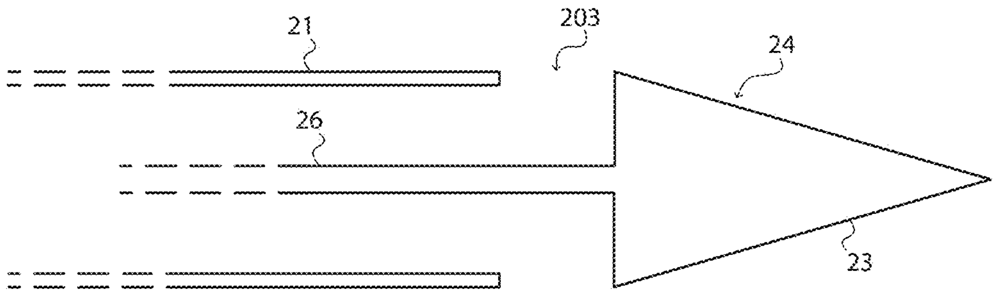
FIG. 1*c* schematically illustrates a needle system in an open state.

The needle system 10 has a closed state and an open state. As illustrated in FIG. 1*b*, the rod tip portion 23 seals, or blocks, the needle opening 203 in the closed state. As illustrated in FIG. 1*c*, the rod tip portion 23 is shifted forward relative to the needle 21 and unseals, or unblocks, the needle opening 203 in the open state. The proximal end 211 of the needle 21 is connected to the actuator body 39 and the proximal end 211 of the needle 21 is open to the cavity 33. The rod 24 is configured to interact with the actuator device 30 such that at a change of volume of the cavity 33, a force is exerted on the rod 24 in a distal direction, setting the needle system 10 in the open state.

For example, in order to set the needle system 10 in the open state, the rod 24 may be configured to interact with a distal wall 37 of the cavity 33. Also or alternatively, in order to set the needle system 10 in the open state, the rod 24 may be configured to interact with a proximal wall 38 of the cavity 33.

Figure 2A:
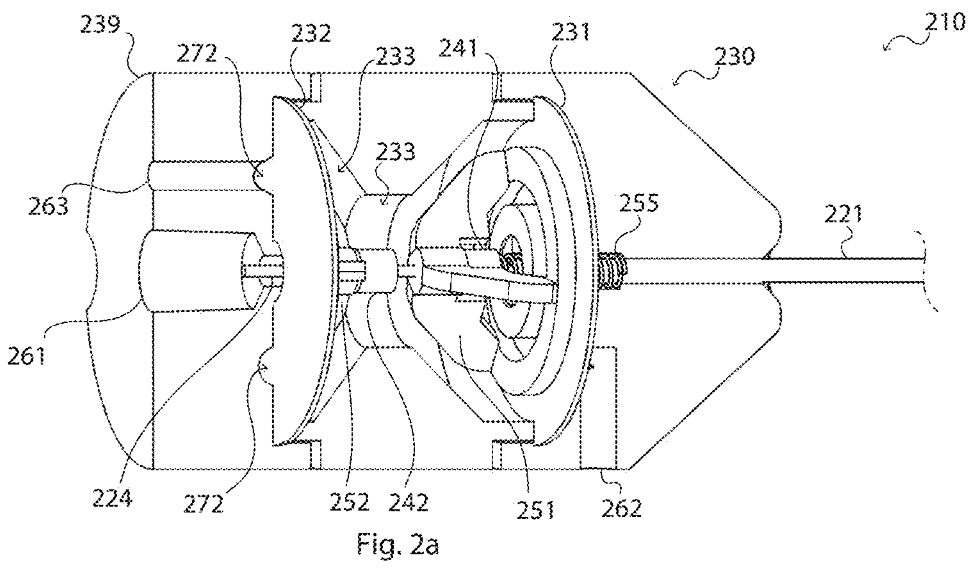
FIGS. 2*a* and 2*b* schematically illustrate a needle system having two membranes, FIG. 3 schematically illustrates cavity dimensions of a needle system, FIG. 4 schematically illustrates a needle system having one membrane, and FIG. 5*a* schematically illustrates a needle system having two membranes, FIG. 5*b* schematically illustrates a needle system having two membranes, FIG. 5*c* schematically illustrates a needle system having two membranes, FIG. 6*a* schematically illustrates a side view of needle system, FIG. 6*b* schematically illustrates a cross-sectional view of the needle system in FIG. 6*a*, FIG. 6*c* schematically illustrates a perspective view of a rod carrier of the needle system in FIG. 6*a* and FIG. 6*b*, and FIG. 6*d* schematically illustrates a cross sectional perspective view of the needle system in FIG. 6*a* and FIG. 6*b*.
Figure 2B:
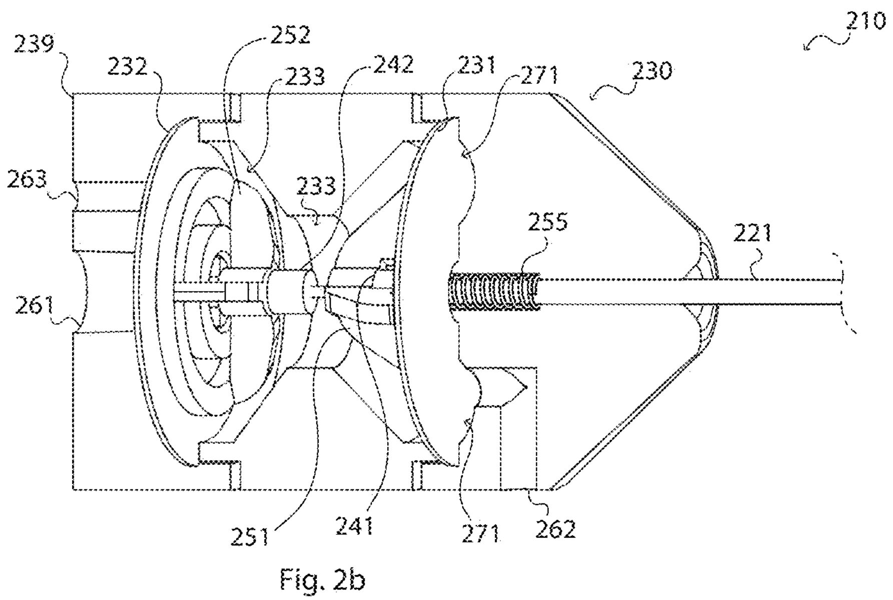

Turning now to FIGS. 2*a-b*, a needle system 210 that is capable of both injection and aspiration will be described in some more detail. The needle system 210 comprises an actuator device 230 comprising a body 239 with a first opening 261 for a fluid transportation device. The actuator device 230 further comprises a distal flexible membrane 231 arranged at a distal end of the cavity 233 and constituting the distal wall of the cavity 233. A proximal flexible membrane 232 is arranged at a proximal end of the cavity 233 and constituting the proximal wall of the cavity 233. The rod 224 is configured to interact with the distal membrane 231 such that when the cavity 233 is pressurized with respect to the outside of the cavity 233, i.e. during an injection procedure, a force is exerted on the rod 224 by the distal membrane 231 in a distal direction, setting the needle system 210 in the open state whereby injection may commence. Furthermore, the rod 224 is also configured to interact with the proximal membrane 232 such that when the cavity 233 is de-pressurized with respect to the outside of the cavity 233, i.e. during an aspiration procedure, a force is exerted on the rod 224 by the proximal membrane 232 in the distal direction, setting the needle system 210 in the open state whereby aspiration may commence.

As illustrated, the actuator device 230 may comprise a distal force transfer unit 251 attached to the distal membrane 231 and a proximal force transfer unit 252 attached to the proximal membrane 232. The function of the force transfer units 251, 252 is to transfer movement of the membranes 231, 232 to the rod 224.The distal force transfer unit 251 is configured to releasably connect to a first protrusion 241 fixed to the rod 224 at a position that is distal in relation to the distal force transfer unit 251. The proximal force transfer unit 252 is configured to releasably connect to a second protrusion 242 fixed to the rod 224 at a position that is distal in relation to the proximal force transfer unit 252. The force transfer units 251, 252 are releasably connected to the rod 224 in that the rod 224 runs freely through a hole in respective force transfer units 251, 252. However, other configurations are foreseen that allow the force transfer units 251, 252 to act upon the rod 224, via the protrusions 241, 242 while at the same time move freely with regard to the rod 224.

In such configurations, the first protrusion 241 is distal in relation to the second protrusion 242. Advantageously, the distal force transfer unit 251 and the proximal force transfer unit 252 may be fixed with or configured as a respective integral part of the distal membrane 231 and the proximal membrane 232.

Furthermore, as illustrated, the distal force transfer unit 251 may be attached to the distal membrane 231 inside the cavity 233 and proximal in relation to the distal membrane 231 and the distal force transfer unit 251 may be configured to transfer a force on the rod 224 in the distal direction via the first protrusion 241. For such a configuration, the proximal force transfer unit 252 is attached to the proximal membrane 232 inside the cavity 233 and distal in relation to the proximal membrane 232, and the proximal force transfer unit 252 is configured to transfer a force on the rod 224 in the distal direction via the second protrusion 242. In such configurations, the first protrusion 241 is distal in relation to the second protrusion 242.

A first hollow 271 may be configured inside the actuator body 239, the first hollow 271 being distal to the distal membrane 231 and outside the cavity 233. The first hollow 271 is configured to allow the distal membrane 231 to flex in the distal direction when the cavity 233 is pressurized. A second opening 262 in the body 239 is then configured to convey ambient pressure to the first hollow 271. A third opening 263 in the body 239 may be configured to convey ambient pressure to the proximal side of the proximal membrane 232 outside the cavity 233, allowing the proximal membrane 232 to flex in the distal direction during aspiration.

Figure 3:
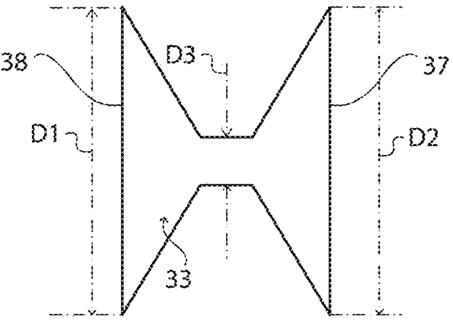

FIG. 3 schematically illustrates how the cavity 233 may be configured in terms of dimensions. That is, the cavity 233 inside the actuator device 230 may have a spatial extent defined as the proximal end of the cavity 233 has a first diameter D1 in a direction perpendicular to the distal and proximal directions. The distal end of the cavity 233 has a second diameter D2 in the direction perpendicular to the distal and proximal directions and a third diameter D3 of the cavity 233, in the direction perpendicular to the distal and proximal directions, at a position between the distal end and the proximal end of the cavity 233 is smaller than the first diameter D1 and smaller than the second diameter D2. Such a configuration enables minimization of the volume of the cavity 233 and thereby minimizing the volume of any fluid that will remain in the cavity 233 subsequent to injection and/or aspiration.

Figure 4:
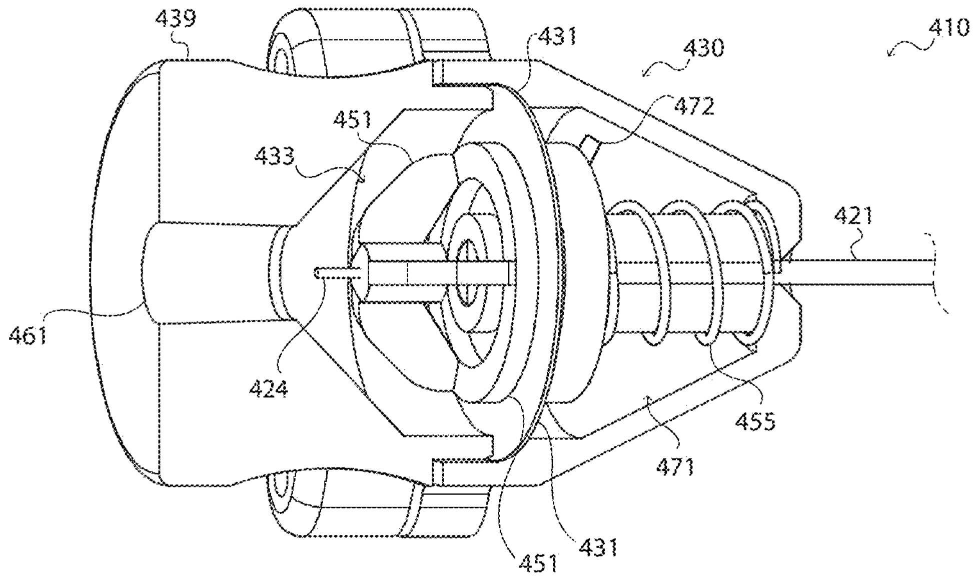

FIG. 4 illustrates an alternative configuration of a needle system 410 that is capable of only injection. The needle system 410 comprises a needle 421 and an actuator device 430. A flexible distal membrane 431 is arranged at a distal end of the cavity 433 and constituting the distal wall of the cavity 433. A rod 424 is configured to interact with the distal membrane 431 such that when the cavity 433 is pressurized with respect to the outside of the cavity 433, a force is exerted on the rod 424 by the distal membrane 431 in a distal direction, setting the needle system 410 in the open state.

As illustrated, the actuator device 430 may comprise a distal force transfer unit 451 attached to the distal membrane 431. Advantageously, the distal force transfer unit 451 is fixed with or is configured as an integral part of the distal membrane 431 and fixed to the rod 424, and its function is to transfer movement of the membrane 431 to the rod 424.

A first hollow 471, open to an outer atmosphere via an opening 472, may be configured inside the actuator body 439, the first hollow 471 being distal to the distal membrane 431 and outside the cavity 433. The first hollow 471 is configured to allow the distal membrane 431 to flex in the distal direction when the cavity 433 is pressurized.

Although not illustrated, a configuration of a needle system that is capable of only aspiration comprises features corresponding to those of the needle system 410, differing only in the fact that it comprises a proximal membrane arranged at a proximal end of the cavity 433 and constituting the proximal wall of the cavity 433. A rod 424 is in such a configuration configured to interact with the proximal membrane 431 such that when the cavity 433 is de-pressurized with respect to the outside of the cavity 433, a force is exerted on the rod 424 by the proximal membrane 431 in a distal direction, setting the needle system 410 in the open state.

Figure 5A:
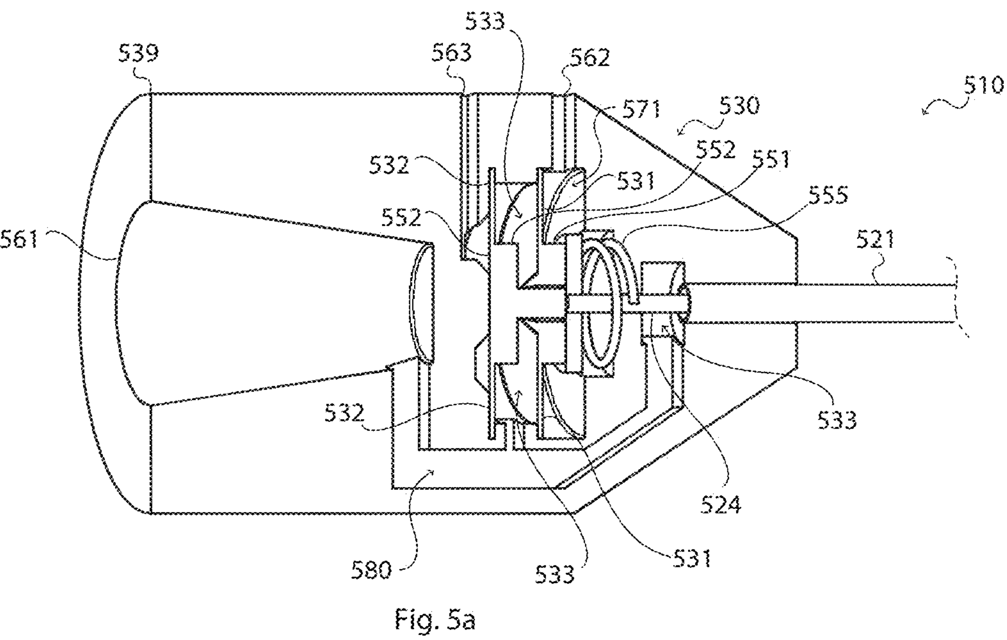

FIG. 5*a* illustrates an alternative configuration of a needle system 510 that is capable of both injection and aspiration. The needle system 510 comprises a needle 521 and an actuator device 530 that comprises a body 539 with a first opening 561 for a fluid transportation device. A distal flexible membrane 531 is arranged at a distal end of a cavity 533 and constituting the distal wall of the cavity 533. A proximal flexible membrane 532 is arranged at a proximal end of the cavity 533 and constituting the proximal wall of the cavity 533. A rod 524 is configured to interact with the distal membrane 531 such that when the cavity 533 is pressurized with respect to the outside of the cavity 533, i.e. during an injection procedure, a force is exerted on the rod 524 by the distal membrane 531 in a distal direction, setting the needle system 510 in the open state whereby injection via the needle 521 may commence. Furthermore, the rod 524 is also configured to interact with the proximal membrane 532 such that when the cavity 533 is de-pressurized with respect to the outside of the cavity 533, i.e. during an aspiration procedure, a force is exerted on the rod 524 by the proximal membrane 532 in the distal direction, setting the needle system 510 in the open state whereby aspiration may commence via the needle 521.

Pressurizing and de-pressurizing of the cavity 533 takes place via the first opening 561 in the body 539 that is configured to interface with a fluid transportation device, as exemplified above. A channel 580 conveys fluid into and out of the cavity 533 as well as into and out of the needle 521. In other words, the channel 580 is configured to convey fluid both into the needle 521 and into the cavity 533 in a "parallel" sense. The cavity 533 may be configured to have a minimal volume while allowing the membranes 531, 532 to flex in the proximal and distal directions. Such a configuration, together with a configuration of the channel 580 such that the volume of channel 580 is minimized, an overall minimization is obtained of the volume of any fluid that will remain in the cavity 533 and the channel 580 subsequent to injection and/or aspiration.

As illustrated, the actuator device 530 may comprise a distal force transfer unit 551 attached to the distal membrane 531 and a proximal force transfer unit 552 attached to the proximal membrane 532. Advantageously, the distal force transfer unit 551 and the proximal force transfer unit 552 are configured as integral parts of the distal membrane 531 and the proximal membrane 532, respectively, and their function is to transfer movement of the membranes 531, 532 to the rod 524 similar to the configurations described above in connection with FIGS. 2*a-c* and 4.

A first hollow 571 may be configured inside the actuator body 539, the first hollow 571 being distal to the distal membrane 531 and outside the cavity 533. The first hollow 571 is configured to allow the distal membrane 531 to flex in the distal direction when the cavity 533 is pressurized. A second opening 562 is then configured to convey ambient pressure to the first hollow 571. A third opening 563 may be configured to convey ambient pressure to the proximal side of the proximal membrane 532 outside the cavity 533, allowing the proximal membrane 532 to flex in the distal direction during aspiration.

Figure 5B:
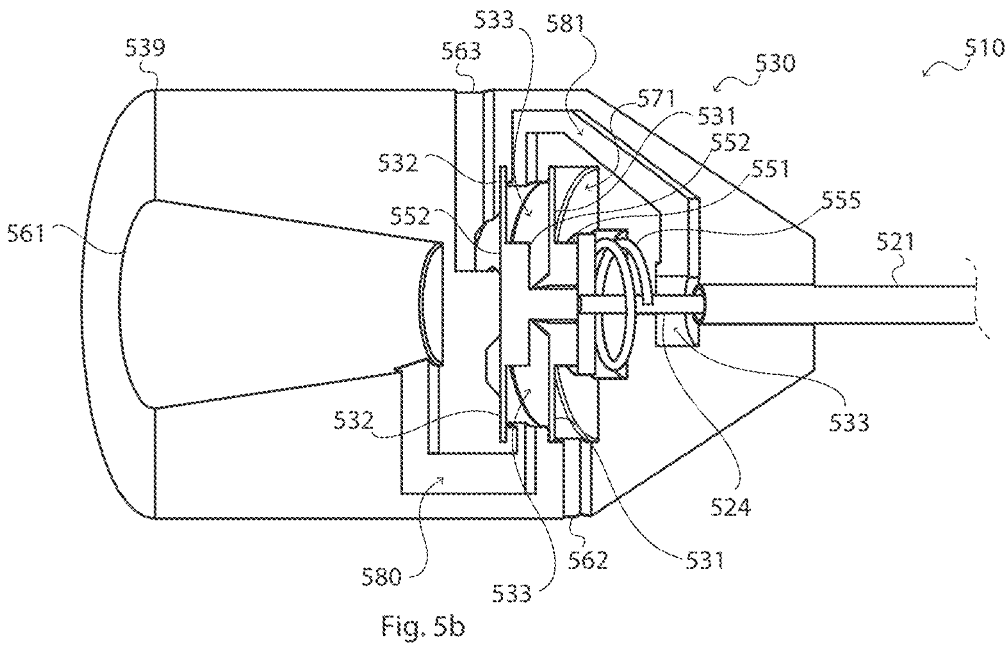

FIG. 5*b* illustrates yet an alternative configuration of a needle system 510 that is capable of both injection and aspiration. The needle system 510 in FIG. 5*b* is similar to the needle system 510 in FIG. 5*a* in that fluid is conveyed from the first opening 561 to the needle 521. The channel 580 extends from the first opening 561 and ends in the cavity 533 at a first position and a second channel 581 extends from the cavity 533 at a second position to the needle 521. In other words, the channel 580 and the second channel 581 are configured to convey fluid into the needle 521 via the cavity 533 in a "sequential" sense. An advantage of such a configuration is that it reduces the risk of air getting into the fluid being injected or aspirated via the channels 580, 581.

Figure 5C:
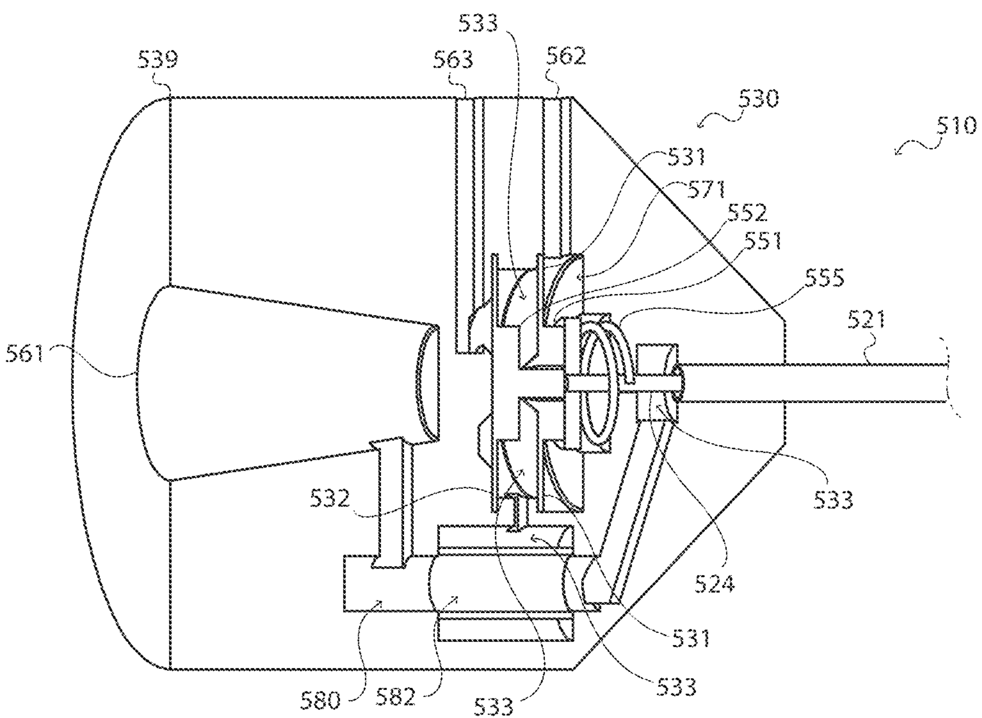

FIG. 5*c* illustrates yet an alternative configuration of a needle system 510 that is capable of both injection and aspiration. The needle system 510 in FIG. 5*c* is similar to the needle system 510 in FIG. 5*a* in that fluid is conveyed from the first opening 561 to the needle 521. The channel 580 extends from the first opening 561 and ends at the needle 521. A part 582 of the channel 580 is configured with flexible, "membrane-like", walls and part of the cavity 533 extends around the flexible part 582 of the channel 580. During injection and aspiration, the flexible part 582 of the channel 580 will expand and contract, respectively, and thereby change the volume of the cavity 533 as defined herein (noting that the cavity 533 is, preferably, filled with a non-compressible medium such as a liquid, in order to facilitate the conveying of the change of volume to the membranes 531, 532). In other words, the channel 580 comprising the flexible part 582 are configured to convey fluid into the needle 521 via the cavity 533 in a "direct"

sense. Such a configuration further reduces, or even minimizes, the risk of air getting into the fluid being injected or aspirated via the channels 580 due to the fact that, when flushed with fluid, there is no contact between fluid and air along the way between the first opening 561 and the needle 521.

As illustrated in FIGS. 2*a-c,* 4 and 5 the actuator device 230, 430, 530 of the needle system 210, 410, 510 may comprise a spring 255, 455, 555 arranged inside the actuator body 239, 439, 539, the spring 255, 455, 555 being arranged to provide a force in the proximal direction on the rod 224, 424, 524 and thereby to bias the needle system 210, 410, 510 in the closed state. As illustrated in FIGS. 2*a-c,* 4 and 5, the spring 255, 455, 555 is arranged distally against an inner surface of the body 239, 439 or form part of the body 539 itself. At a proximal end, the spring 255, 455, 555 abuts the distal force transfer unit 251, 451, 551 and thereby provides a biasing force in the proximal direction. The effect of such a configuration is that the tip portion 23 of the rod 224, 424, 524 is held firmly against the needle opening 203. Such a configuration prevents any gap to open up between the needle opening 203 and the tip portion 23 of the rod 224, 424, 524 during insertion and retraction of the needle 221, 421, 521.

It is to be noted that such a spring 255, 455, 555 is to be interpreted broadly and it includes any device capable of providing a spring force or a force similar to a spring force, for example an injection moulded plastic detail, and although the present disclosure exemplifies spring by a coiled spring, it is to be understood that any other device may be used that provides a corresponding force.

FIGS. 6*a-d* illustrate yet an alternative configuration of a needle system 610 that is capable of both injection and aspiration. Similar to the needle systems described above, the needle system 610 comprises a needle arrangement 620 and an actuator device 630. The needle arrangement 620 comprises a needle 621 having a proximal end 611 and a distal end 612 and having a needle opening 603 at the distal end 612 of the needle 621. A rod 624 has a proximal end 625 and a distal end 622 and a length that is greater than the length of the needle 621. The rod 624 comprises an elongated rod shaft portion 626 configured to fit inside the needle 621 and a rod tip portion 623 located at the distal end 622 of the rod 624.

The actuator device 630 comprises an actuator body 639 comprising a cavity 633. A first opening 661 in the actuator body 639 is configured to interface with a fluid transportation device (not illustrated in FIGS. 6*a-d*) to allow fluid into and/or out of the cavity 633 and thereby allowing fluid to be injected and/or aspirated through the needle 621.

As for the systems described above, the needle system 610 has a closed state and an open state, where the rod tip portion 623 seals, or blocks, the needle opening 603 in the closed state, and the rod tip portion 623 is shifted forward relative to the needle 621 and unseals, or unblocks, the needle opening 603 in the open state.

The proximal end 611 of the needle 621 is connected to the actuator body 639 and the proximal end 611 of the needle 621 is open to the cavity 633. The rod 624 is configured to interact with the actuator device 630 such that at a change of volume of the cavity 633 a force is exerted on the rod 624 in a distal direction, setting the needle system 610 in the open state.

In some more detail, a flexible bellows 680, arranged within the actuator body 639, is configured with a hollow middle section that constitutes the cavity 633. A distal part of the bellows 680 forms a flexible distal bellows wall 681 and a proximal part of the bellows 680 forms a flexible proximal bellows wall 682. An opening 683 in the distal bellows wall 681 is open to the first opening 661 and an opening 684 in the proximal bellows wall 682 is open to the needle 621. A rigid distance device 695 is arranged, e.g., in the form of an annular tube between the circumferential edges of the distal bellows wall 681 and the proximal bellows wall 682. Such an arrangement prevents distal and proximal movement of the circumferential edges of the distal bellows wall 681 and the proximal bellows wall 682. Other means of preventing such movement may include attachment of the circumferential edges directly to the inside wall of the actuator body 639.

The rod 624 is fixed to a rod carrier 690 that is arranged partly within the cavity 633 inside the bellows 680. The rod carrier 690 comprises a distal end 691 and a proximal end 692. The distal end 691 of the rod carrier 690 is shaped with a flange 694 that is arranged distally in relation to the distal bellows wall 681. The proximal end 692 of the rod carrier 690 is arranged distally in relation to the proximal bellows wall 682. Grooves 693 in the rod carrier 690 are arranged to avoid blocking flow of fluid being conveyed via the bellows 680 during injection and aspiration between the needle 621 and the first opening 661.

Figure 6A:
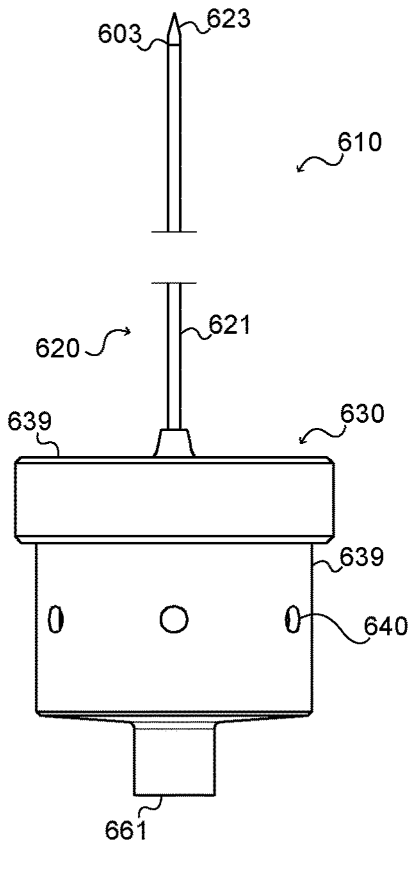
Figure 6B:
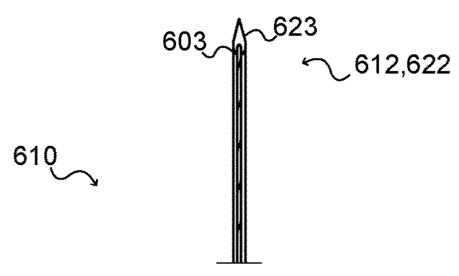
Figure 6B:
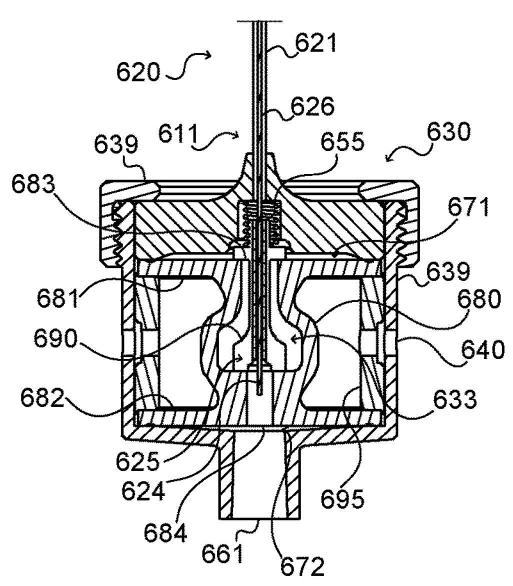
Figure 6C:
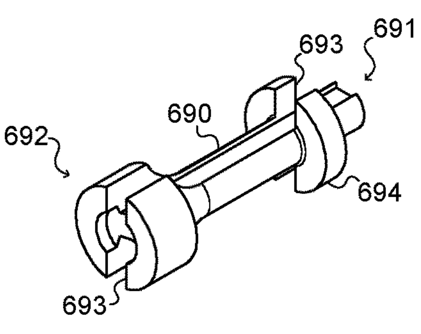
Figure 6D:
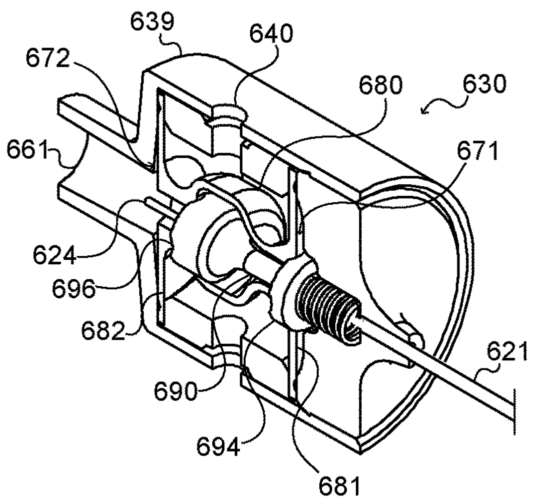

Similar to the examples described above, a spring 655 is arranged inside the actuator body 639, the spring 655 being arranged to provide a force in the proximal direction on the rod 624 and thereby to bias the needle system 610 in the closed state. As illustrated in FIGS. 6*b* and 6*d*, the spring 655 is arranged distally against an inner surface of the body 639, or it may form part of the body 639 itself. At a proximal end, the spring 655 abuts the distal end 693 of the rod carrier 690 and thereby provides a biasing force in the proximal direction. The effect of such a configuration is that the tip portion 623 of the rod 624 is held firmly against the needle opening 603.

In an injection scenario, fluid is introduced under a certain pressure from, e.g., a syringe into the bellows 680 via the first opening 661 and the opening 684 in the proximal bellows wall 682. While filling the cavity 633 of the bellows 680, the pressure from the fluid provides a force in the distal direction upon the proximal bellows wall 682. The outside of the bellows 680 is open to atmospheric pressure, e.g. as exemplified in FIGS. 6*a*, 6*b* and 6*c* via holes 640 in the actuator body 639 and, as a consequence, the proximal bellows wall 682 will flex in the distal direction due to the introduction of the fluid. The distal flexing of the proximal bellows wall 682 provides a force upon the proximal end 692 of the rod carrier 690, resulting in that the rod 624 is forced in the distal direction and thus setting the needle system 610 in the open state and fluid inside the cavity 633 may flow out through the needle opening 603.

In an aspiration scenario, a relative under-pressure is created inside the bellows 680, i.e. inside the cavity 633 by, e.g., a syringe via the first opening 661 and the opening 684 in the proximal bellows wall 682. Due to the fact that the outside of the bellows 680 is open to atmospheric pressure, e.g. as exemplified in FIGS. 6*a*, 6*b* and 6*c* via holes 640 in the actuator body 639, a consequence of the under-pressure inside the bellows 680 is that the bellows 680 will expand in the distal and proximal direction. As a consequence of this expansion of the bellows 680 the distal bellows wall 681 will flex in the distal direction (and the proximal bellows wall 682 will flex in the proximal direction). As illustrated in FIGS. 6*b* and 6*d*, this distally directed flexing of the distal bellows wall 681 is allowed by a hollow 671 that is formed between the distal bellows wall 681 and the actuator body 639, similar to the examples described above. (The proximally directed flexing of the proximal bellows wall 682 is allowed by a hollow 672 that is formed between the proximal bellows wall 682 and the actuator body 639.) As a consequence of the distal flexing of the distal bellows wall 681, the flange 694 of the distal end 691 of the rod carrier 690 is forced by the distal bellows wall 681 in the distal direction (the flange 694 being wider than the opening 683 in the distal bellows wall 681) and thus setting the needle system 610 in the open state and the under-pressure inside the cavity 633 may result in aspiration of fluid through the needle opening 603 via the needle 624 and via the cavity 633 and out through the first opening 661 and into, e.g., the syringe.

It is to be noted in FIG. 6*d* that the rod carrier 600 lacks grooves but is configured at the proximal end with notches 696 that allow fluid being conveyed via the bellows 680 during injection and aspiration between the needle 621 and the first opening 661.

The invention claimed is:

1. A needle system, comprising:

a needle arrangement including a needle having a first length between a proximal end and a distal end, the distal end of the needle having a needle opening, and a rod having a second length between a proximal rod end and a distal rod end, the second length being greater than the first length, wherein the rod includes an elongated rod shaft portion configured to fit inside the needle and a rod tip portion located at the distal rod end; and an actuator device, comprising an actuator body defining a cavity having a proximal wall at a proximal end, a distal wall at a distal end, and a first opening configured for fluid connection to a fluid transportation device, to allow fluid to flow into and/or out of the cavity;

wherein the needle system has a closed state and an open state, wherein the rod tip portion blocks the needle opening in the closed state, and wherein the rod tip portion is shifted distally relative to the needle to unblock the needle opening in the open state;

wherein the proximal end of the needle is connected to the actuator body and is open to the cavity; and wherein the rod is configured to interact with the actuator device such that , when the cavity is de-pressurized, the volume of the cavity changes, and a first force is exerted on the rod by the actuator device in a distal direction, setting the needle system in the open state, thereby allowing fluid to be aspirated through the needle.

2. The needle system of claim 1, wherein a flexible bellows arranged within the actuator body forms the cavity, and the bellows comprises the distal wall in the form of a distal bellows wall and the proximal wall in the form of a proximal bellows wall and wherein a rod carrier to which the rod is attached is arranged partly within the cavity, and the rod is configured to interact via the rod carrier with the distal wall and the proximal wall of the bellows such that, during both injection and aspiration, the rod is forced in the distal direction setting the needle system in the open state.

3. The needle system of claim 1, wherein the rod is configured to interact with the distal wall of the cavity.

4. The needle system of claim 1, wherein the rod is configured to interact with the proximal wall of the cavity.

5. The needle system of claim 1, wherein the proximal wall of the cavity comprises a flexible proximal membrane; and wherein the rod is configured to interact with the proximal membrane such that when the cavity is de-pressurized, the volume of the cavity changes, and the first force is exerted on the rod by the proximal membrane in the distal direction, setting the needle system in the open state.

6. The needle system of claim 5, wherein the actuator device further includes a proximal force transfer unit attached to the proximal membrane and configured to exert the first force on the rod.

7. The needle system of claim 5, wherein the actuator body further comprises:

a second opening configured to convey ambient pressure to a proximal side of the proximal membrane from outside the cavity.

8. The needle system of claim 1, wherein the actuator device further comprises:

a spring arranged inside the actuator body and configured to provide a force in the proximal direction on the rod and thereby to bias the needle system in the closed state.

9. The needle system of claim 1, wherein:

the proximal end of the cavity has a first diameter in a direction perpendicular to the distal and proximal directions;

the distal end of the cavity has a second diameter in the direction perpendicular to the distal and proximal directions; and the cavity has a third diameter, in the direction perpendicular to the distal and proximal directions, at a position between the distal end and the proximal end of the cavity, the third diameter being smaller than the first diameter and smaller than the second diameter.

10. The needle system of claim 1, wherein in the rod is configured to interact with the actuator device such that when the cavity is pressurized, the volume of the cavity changes, and a second force is exerted on the rod by the actuator device in the distal direction, setting the needle system in the open state, thereby allowing fluid to be injected through the needle.

11. The needle system of claim 10, wherein the distal wall of the cavity comprises a flexible distal membrane, and wherein the rod is configured to interact with the distal membrane such that when the cavity is pressurized, the volume of the cavity changes, and the second force is exerted on the rod by the distal membrane in the distal direction, setting the needle system in the open state.

12. The needle system of claim 11, wherein the actuator device further comprises a distal force transfer unit attached to the distal membrane and configured to exert the second force on the rod.

13. The needle system of claim 11, wherein the actuator body further comprises:

a hollow inside the actuator body, distal to the distal membrane and outside the cavity, the hollow being configured to allow the distal membrane to flex in the distal direction when the cavity is pressurized; and a second opening configured to convey ambient pressure to the hollow.

14. The needle system of claim 10, wherein the proximal wall of the cavity comprises a flexible proximal membrane and the distal wall comprises a flexible distal membrane;

wherein the rod is configured to interact with the distal membrane such that when the cavity is pressurized, the volume of the cavity changes, and the second force is exerted on the rod by the distal membrane in the distal direction, setting the needle system in the open state; and wherein the rod is configured to interact with the proximal membrane such that when the cavity is de-pressurized, the volume of the cavity changes and the first force is exerted on the rod by the proximal membrane in the distal direction, setting the needle system in the open state.

15. The needle system of claim 14, wherein the actuator device further comprises:

a distal force transfer unit attached to the distal membrane; and a proximal force transfer unit attached to the proximal membrane;

wherein the distal force transfer unit is configured to releasably connect to the rod at a position that is distal in relation to the distal force transfer unit; and wherein the proximal force transfer unit is configured to releasably connect to the rod at a position that is distal in relation to the proximal force transfer unit.

16. The needle system of claim 15, wherein the distal force transfer unit is attached to the distal membrane inside the cavity and proximal in relation to the distal membrane and is configured to transfer the first force on the rod in the distal direction; and wherein the proximal force transfer unit is attached to the proximal membrane inside the cavity and distal in relation to the proximal membrane and is configured to transfer the second force on the rod in the distal direction.

17. The needle system of claim 1, wherein the actuator device comprises a first channel configured to convey fluid between the first opening and the cavity, and further comprises a second channel configured to convey fluid between a second opening of the cavity and the needle.

18. The needle system of claim 17, wherein the first channel comprises a flexible part inside the cavity.

* * * * *